United States Patent [19]
Kume et al.

[11] 4,317,725
[45] Mar. 2, 1982

[54] PORTABLE ARTIFICIAL KIDNEY WITH SEPARABLE PARTS

[75] Inventors: Tadashi Kume, Tokyo; Yoshitsugu Fujimori, Tokorozawa; Isamu Inoh, Tokyo, all of Japan

[73] Assignee: Honda Giken Kogyo Kabushiki Kaisha, Tokyo, Japan

[21] Appl. No.: 47,998

[22] Filed: Jun. 13, 1979

[30] Foreign Application Priority Data

Jun. 15, 1978 [JP] Japan .................................. 53/71526
Jun. 15, 1978 [JP] Japan .................................. 53/71527

[51] Int. Cl.³ .......................................... B01D 31/00
[52] U.S. Cl. .................................. 210/235; 210/238; 210/321.3
[58] Field of Search ....... 210/321 A, 321 B, DIG. 23, 210/234, 235, 238; 128/214 B, DIG. 3

[56] References Cited

U.S. PATENT DOCUMENTS

| 3,814,249 | 6/1974 | Eaton | 210/321 B |
| 4,083,777 | 4/1978 | Hutchinsson | 210/321 B |

FOREIGN PATENT DOCUMENTS

| 2125101 | 1/1972 | Fed. Rep. of Germany | 210/321.3 |
| 2235203 | 2/1974 | Fed. Rep. of Germany | 210/321.3 |
| 2740062 | 9/1978 | Fed. Rep. of Germany | 210/321.3 |
| 353231 | 3/1973 | Sweden |
| 73079097 | 5/1973 | Sweden |

*Primary Examiner*—Frank A. Spear, Jr.
*Attorney, Agent, or Firm*—Haseltine and Lake

[57] ABSTRACT

Artificial kidney apparatus comprising a blood circulation system including a dialyzer and a blood pump interposed in a blood circuit connectable with blood vessels of a patient, the blood circulation section being contained together with a drive motor for the blood pump and an electrical supply source thereof in a single casing to form a portable unit. The unit has connection openings for detachable connection with corresponding connection openings of a dialyzing liquid circuit of a dialyzing liquid circulation section. Respective valves are provided in the openings which are normally closed but which when the sections are coupled are opened to provide intercommunication. In a modification a portable container freely contains a blood circulation section and a dialyzing liquid circulation section. A dialyzing liquid supply section is contained within the portable container in the interior thereof not taken up by the blood circulation section and the dialyzing liquid circulation section. An elastic bag can be mounted in the portable container to contain the dialyzing liquid in liquid-tight relation therein.

5 Claims, 7 Drawing Figures

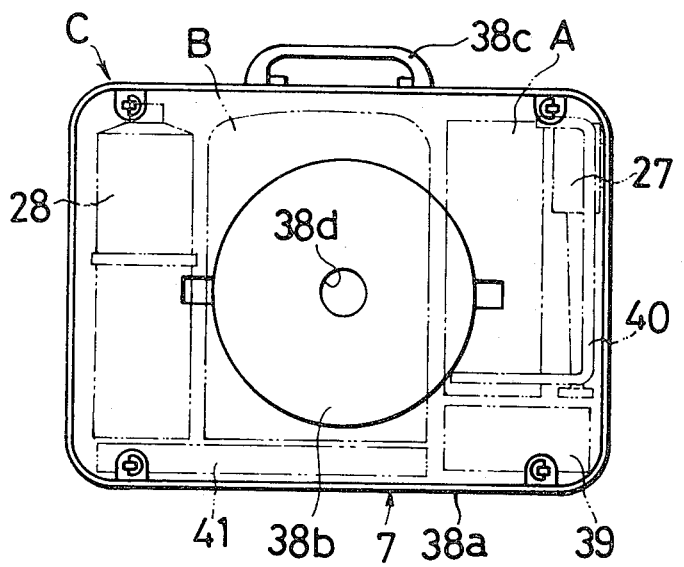
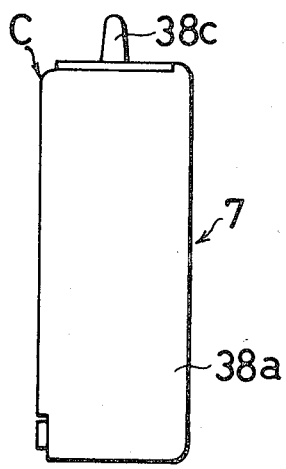
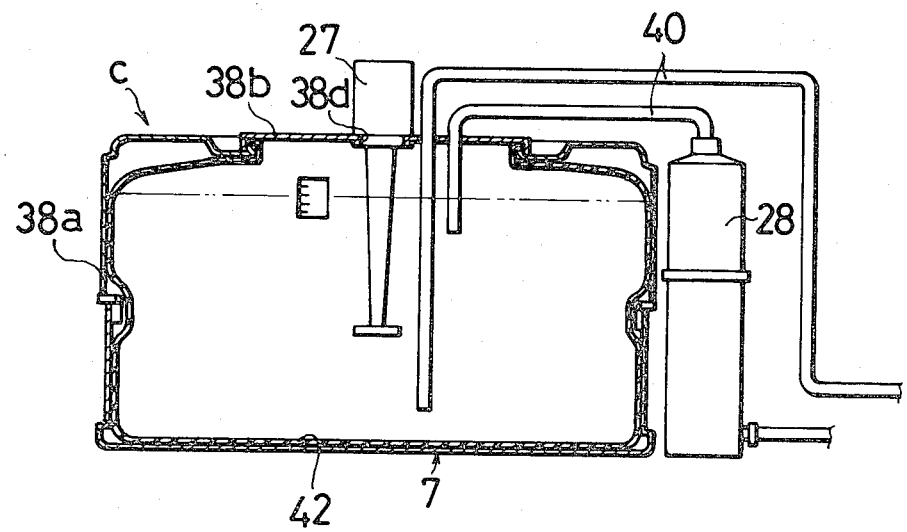

PORTABLE ARTIFICIAL KIDNEY WITH SEPARABLE PARTS

FIELD OF THE INVENTION

This invention relates to a portable artificial kidney with separable parts for substitution for the normal kidney function of a human body.

PRIOR ART

Known in the art is an apparatus of this type in which a blood circulation section, including a dialyzer and a blood pump interposed in a blood circulation circuit, is adapted to be connected to a dialyzing liquid circuit of a dialyzing liquid circulation section. This conventional type of apparatus, however, is large in size and weight, is fixedly installed on a floor or the like, and respective circulation circuits are large in volume.

Accordingly, when a patient is connected to the apparatus for medical treatment, the patient is restricted in mobility for a comparatively long period of time, for instance, for five to six hours, and cannot be released from the apparatus until the medical treatment is completed. Furthermore, in the event of an emergency such as fire, earthquake, power loss or the like, the patient must be disconnected from the apparatus, and, consequently a large amount of blood remains in the blood circulation circuit, thus leading to waste of blood in that the blood cannot be reused.

SUMMARY OF THE INVENTION

An object of the invention is to provide an artificial kidney which is free from the above inconveniences.

According to the present invention, the artificial kidney comprises a blood circulation section incorporating a dialyzer and a blood pump contained together with a driving motor for the blood pump and an electric source therefor, in a single casing so that a portable unit is formed, said portable unit being detachable from a second unit incorporating a dialyzing liquid circuit of a dialyzing liquid circulation section.

It is a feature of the invention that the apparatus is of comparatively small-size so that it can be carried freely, as desired, by a patient and can be used at any desired place.

Another object of the invention is to provide an apparatus meeting this requirement in which a dialyzing liquid supply tank constituting is formed as a portable container, and the blood circulation section and the dialyzing liquid circulation section are contained therein for transportation, and are freely removable therefrom for use.

BRIEF DESCRIPTION OF THE FIGURES OF THE DRAWING

FIG. 5 is a front view of one embodiment of a portable unit incorporating the artificial kidney of this invention.

FIG. 6 is a side view thereof.

FIG. 7 is a side view, partly in section, of a casing of the unit of FIG. 5 in its condition of use.

DETAILED DESCRIPTION

Figure 1:
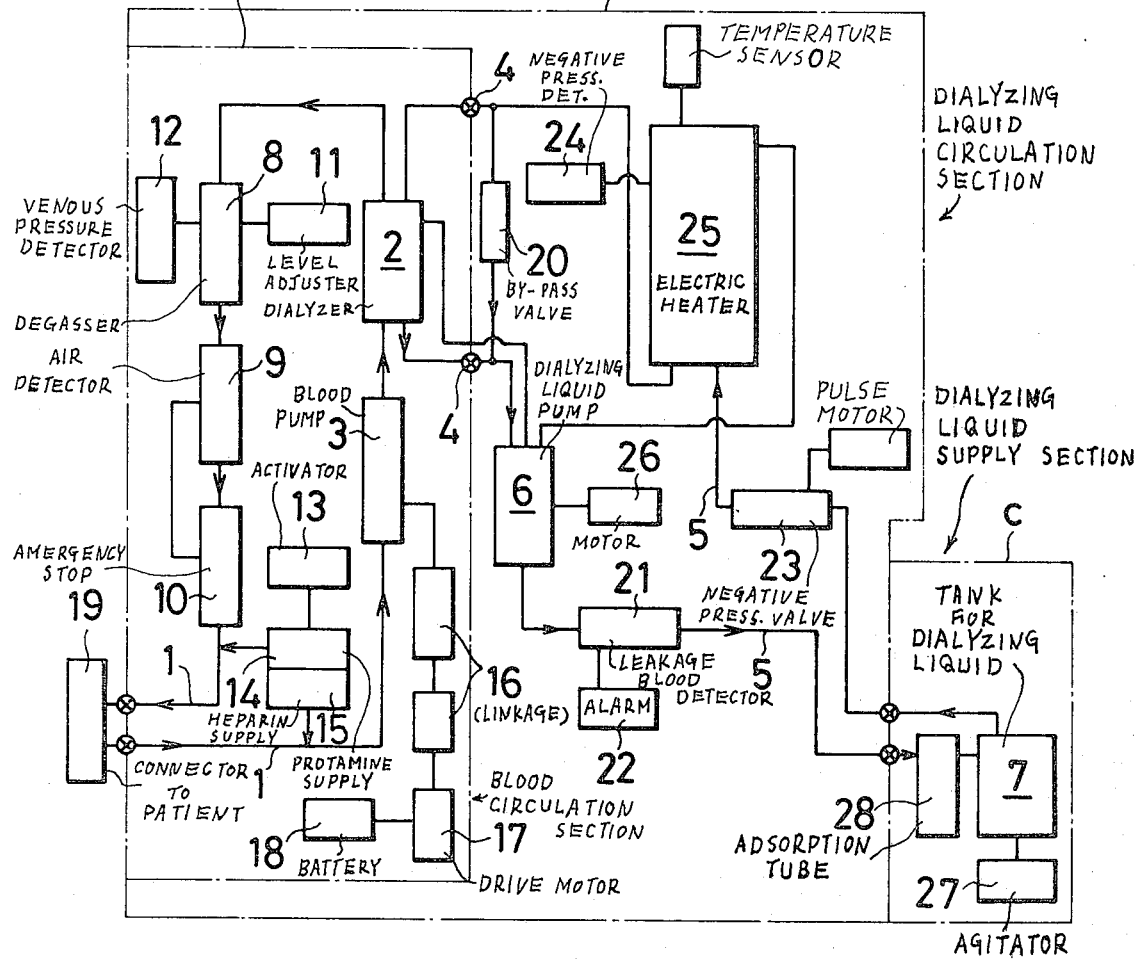
FIG. 1 is a circuit diagram of an artificial kidney according to the present invention.

Referring to FIG. 1 of the drawings, the artificial kidney of the present invention comprises, a blood circulation section a, a dialyzing liquid circulation section b, and a dialyzing liquid supply section c. The blood circulation section a is so constructed that a dialyzer 2 and a blood pump 3 are interposed in a blood circulation circuit 1 which is connectable to blood vessels of a patient. The dialyzing liquid circulation section b is so constructed that a dialyzing liquid pump 6 is interposed in a dialyzing liquid circuit 5 connected to connection openings 4 of the dialyzer 2. The dialyzing liquid supply section c is composed of a dialyzing liquid tank 7 connected to other ends of the circuit 5.

The blood circulation circuit 1 is provided also with a degassing means 8, an air detecting means 9 and an emergency stop means 10. Additionally, the blood circulation circuit 1 includes a level adjusting means 11, a venous pressure detecting means 12, and a protamine supply section 14 and a heparin supply section 15 which are connected to an actuating means 13. The blood pump 3 is provided with a driving motor 17 connected thereto through a linkage means 16 comprising a rocker arm and a cam, and the motor 17 is driven from an electric source 18 such as a battery or the like. Numeral 19 denotes a connector shunt at which the blood circulation circuit 1 is connected to the blood vessels of a patient.

The dialyzing liquid circuit 5 is provided with a by-pass valve 20, a blood leakage detecting means 21, an alarm means 22 connected to detecting means 21, a negative pressure valve 23, a negative pressure detecting means 24, and an electric heater 25. Furthermore, the pump 6 is provided with a driving motor 26 connected thereto. The dialyzing liquid tank 7 has an agitator 27, and has an adsorption tube 28 located in the return conduit to the tank.

The artificial kidney described to this point is not especially different in concept from the conventional apparatus.

Figure 2:
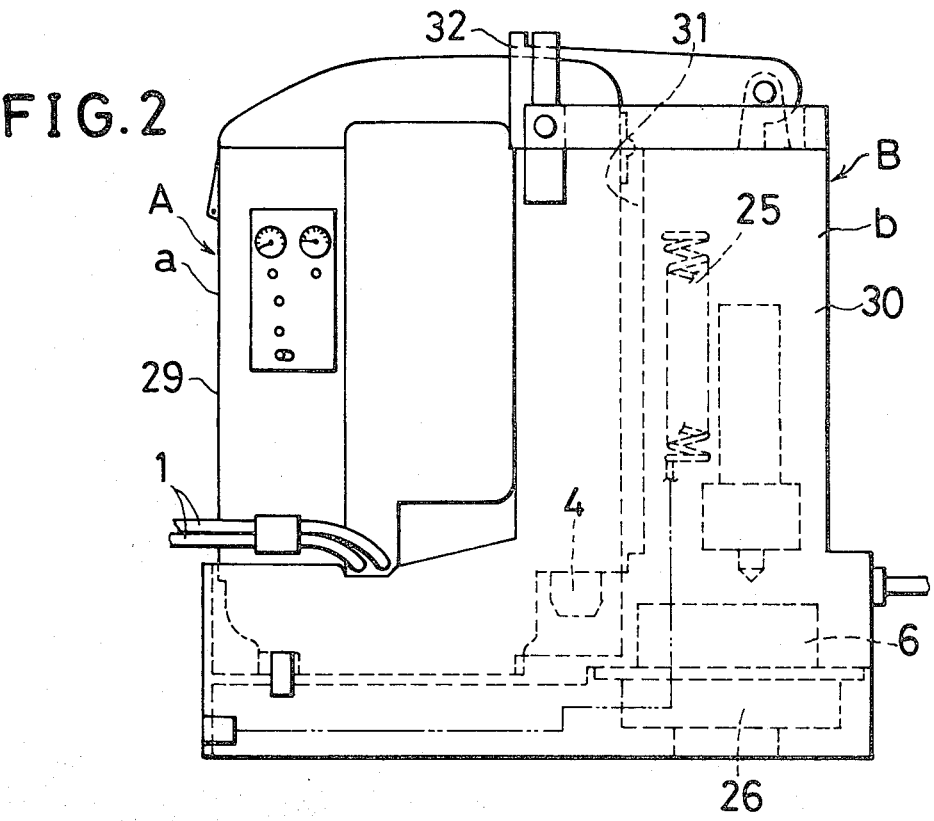
FIG. 2 is a side view of an artificial kidney according to the present invention showing the units thereof in an interconnected condition.
Figure 3:
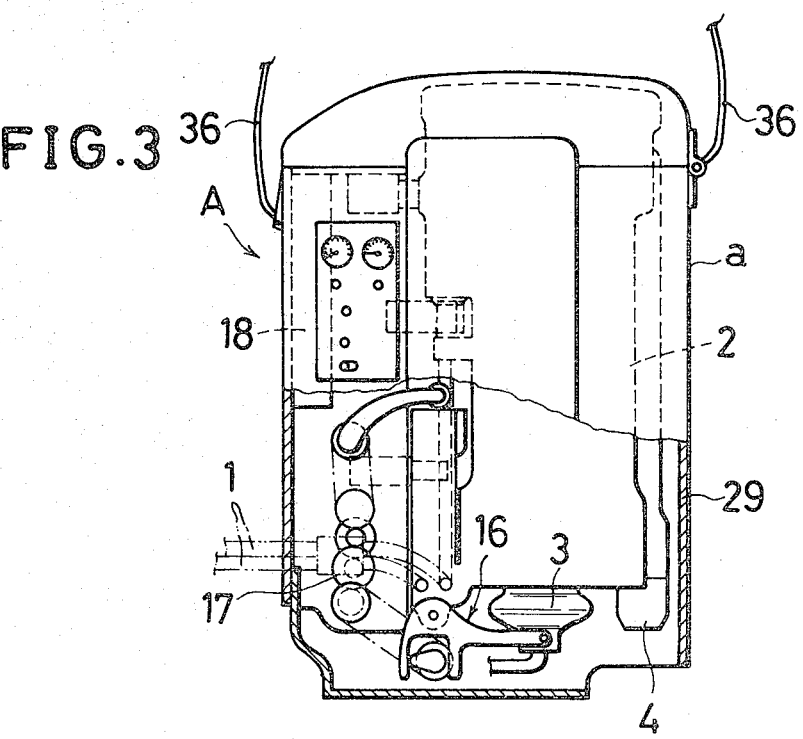
FIG. 3 is a side view, partly broken away and in section, of one of the units of the artificial kidney when separated from the other of the units.

According to this invention, the blood circulation section a, together with the driving motor 17 and the electric source 18, is contained in a single common casing 29, thus providing a comparatively small-sized portable unit A as shown in FIGS. 2 and 3. The unit A is connectable to the circuit 5 of the dialyzing liquid circulation section b via the connection members 4. Similarly, the dialyzing liquid circulation section b, together with the driving motor 26 of the pump 6, is contained in a single common casing 30 so that there is formed a unit B. The unit B is comparatively large in size and is placed on a floor or other surface. The unit B is formed at the front surface thereof with a receiving recess 31, so that the unit A can be introduced into and placed on the unit B. Additionally, as occasion demands, the two units A, B may be interlocked by a locking member 32.

The connection of the blood circulation circuit 1 to the dialyzing liquid circuit 5 is made automatically as the unit A is placed on the unit B.

Figure 4:
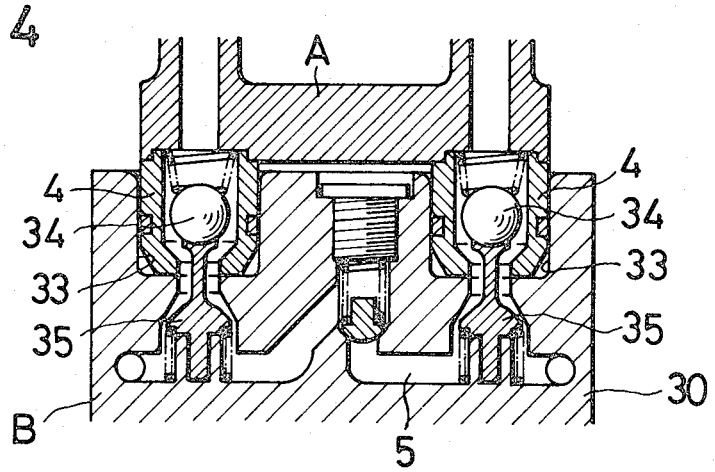
FIG. 4 is an enlarged sectional view of connection members of the unit in FIG. 3.

Namely, as shown clearly in FIG. 4, the connection members 4 project downwards and are detachably inserted into respective openings 33 at the end portions of the circuit 5, the openings 33 being formed in an upper surface of the unit B. The connection members 4 each incorporate valves 34 of the ordinarily closed type which are displaced to open automatically by respective opposed valves 35 of ordinarily closed type provided in the respective openings 33. When the unit A is separated from the unit B, the respective connection members 4 and the respective members 33 are automatically closed by their associated valves 34 and 35 so as to prevent any leakage of the interior liquids. The unit A may be provided with a carrying belt 36, as illustrated.

The operation of the apparatus is as follows:

Under normal conditions, the unit A is introduced into and placed on the unit B as shown in FIG. 2, and thereby the unit A is connected to unit B at the connection members 4. Additionally, the unit B is connected to a supply unit C incorporating the dialyzing liquid supply section c. Thus, if in this condition the dialyzer is connected at the blood circuit 1 to the blood-vessels of a patient, purification of the blood can be effected in almost the same manner as in the conventional apparatus. If, during the course of this operation, the patient must leave the area of the apparatus, the unit A is separated from the unit B, and the patient can leave while carrying the unit A with him. At that time, the patient remains connected to the blood circuit 1 and the circulation of the blood is continued by the pump 3. Thus, no inconvenience is brought about. Thereafter, when the patient has returned to the original location, the unit A is again connected to the unit B, and thus the apparatus is returned to its original condition and the medical treatment is resumed.

Thus, the patient can move at will, while carrying the unit A with him, which eliminates the disadvantage that the patient is bound to a fixed position for a long time. Additionally, as the blood in the blood circuit undergoes continuous circulation at the time the unit A is removed from the unit B the waste of blood as caused in the conventional apparatus is eliminated.

According to another feature of this invention, the supply unit C is constructed to be portable.

Namely, the tank 7 constituting the main portion of the supply unit C is formed as a portable casing 38 comprising a main casing 38a and a cover member 38b as shown in FIGS. 5 and 6. The portable container can be carried by means of a handle 38c. The units A and B are contained in the casing 38a and are freely removable therefrom. Numeral 38d denotes a window cover at the center opening of the cover member 38b. The units A, B are contained in the main casing 38a in their mutually disassembled condition. Additionally, contained within the casing 38a are the agitator 27 and the adsorption tube 28, together with additional parts, such as, for instance, accessories 39, piping tubes 40, a physiological saline container 41 and the like.

Casing 38, after all the elements are removed therefrom, serves as the tank 7, the dialyzing liquid being charged therein. This condition is shown in FIG. 7. It is preferable in this case that the main casing 38a and cover member 38b are made telescopic so as to be convertible into an expanded large-sized condition from a contracted small-sized carrying condition, so that a comparatively large amount of dialyzing liquid, for instance, 30 liters thereof, can be charged therein. A liquid-tight rubber bag 42 is attached to the interior surface of the cover member 38b, the rubber bag 42 constituting the interior surface of the tank 7.

In use, the tank 7 is placed with the cover member 38b directed upwards, and the agitator 27 and the piping tubes 40 are attached thereto by insertion through the cover member 38b, and the adsorption tube 28 is positioned at the side thereof. Thereby, the dialyzing liquid circulation supply section c may be established as a whole. Accordingly, if the dialyzing liquid circulation section b and the blood circulation section a are connected thereto in order, an apparatus is established in use condition for a medical treatment.

Thus, according to this invention, the dialyzing liquid tank constituting the main portion of the dialyzing liquid supply section is formed as a bag located within a portable container. The blood circulation section and the dialyzing liquid circulation section are transportable within the container and freely removable therefrom so that the entire apparatus can be made smaller in size, and simple and easy to carry.

What is claimed is:

1. In an artificial kidney apparatus of the type including a blood circulation section comprising a blood circuit connectable with blood vessels of a patient, a dialyser and a blood pump interposed in said blood circuit, drive motor means for the blood pump, and electrical supply means for said motor means, and, a dialyzing liquid circulation section comprising a dialyzing liquid circuit, a dialyzing liquid pump, and drive motor means for the dialyzing liquid pump, the improvement comprising:

a first casing containing said blood circulation section inclusive of said blood circuit, said dialyser, said blood pump, said motor means, and said electrical supply means to form an integral portable unit;

a second casing from which said first casing is readily detachable and which contains said dialyzing liquid circulation unit; and means for operatively coupling and uncoupling said portable unit with said dialyzing liquid circulation unit to automatically connect and disconnect said blood circulation section and said dialyzing liquid circulation section;

said means for operatively coupling and uncoupling said portable unit with said dialyzing liquid circulation unit including valve means for connecting the dialyzer of said blood circulation section to said dialyzing liquid circuit when said units are coupled together and for disconnecting said dialyser from said dialyzing liquid circuit when said units are uncoupled;

said valve means comprising first normally closed valve elements located in said portable unit, and second normally closed valve elements located in said dialyzing liquid circulation unit, said first and second valve elements including cooperating parts to open said valve elements when said units are coupled together;

said blood circulation unit being provided with openings in which said first valve elements are mounted, and said dialyzing liquid circulation unit having openings in which said second valve elements are mounted, said openings being placed in communication with one another with said valve elements opened when said units are coupled together.

2. Artificial kidney apparatus as claimed in claim 1, including a portable container in which said blood circulation section and said dialyzing liquid circulation section are contained as to be freely removable, said dialyzing liquid supply section comprising a dialyzing liquid tank constituted by said portable container.

3. An artificial kidney apparatus as claimed in claim 2 wherein said portable container is capable of expansion and contraction in at least two stages, so that the container can be carried in a contracted small-size state and can be used as the tank in an expanded large-size state.

4. An artificial kidney apparatus as claimed in claim 2 comprising an elastic bag mounted in said portable container at the inner surface thereof for containing dialyzing liquid.

5. An artificial kidney apparatus as claimed in claim 2 comprising handle means on said portable container.

* * * * *